United States Patent [19]
Fowler et al.

[11] Patent Number: 5,885,603
[45] Date of Patent: Mar. 23, 1999

[54] INSECTICIDAL MATRIX AND PROCESS FOR PREPARATION THEREOF

[75] Inventors: Jeffrey D. Fowler; Benjamin E. Feinstein, both of Mountain View, Calif.

[73] Assignee: Novartis Corporation, Summit, N.J.

[21] Appl. No.: 908,290

[22] Filed: Aug. 7, 1997

Related U.S. Application Data

[63] Continuation of Ser. No. 654,512, Jun. 12, 1996, Pat. No. 5,851,545.

[60] Provisional application No. 60/003,336, Aug. 25, 1995.

[51] Int. Cl.$^6$ .................................................. A01N 25/28
[52] U.S. Cl. ......................... 424/405; 424/408; 424/409; 424/417; 424/421; 424/485; 424/491; 424/496; 424/497; 424/499; 424/500; 424/501
[58] Field of Search .................................... 424/405, 406, 424/408, 409, 417–419, 421, 485–491, 496, 497, 499–501, 93.1, 93.3, 93.461

[56] References Cited

U.S. PATENT DOCUMENTS

| | | | |
|---|---|---|---|
| 3,541,203 | 11/1970 | Fogle et al. | 424/17 |
| 4,000,258 | 12/1976 | Shieh et al. | 424/93 |
| 4,844,896 | 7/1989 | Bohm et al. | 424/92 |
| 4,902,507 | 2/1990 | Morris et al. | 424/93 |
| 5,142,817 | 9/1992 | Rolf | 47/24 |
| 5,143,905 | 9/1992 | Sivasubramanian et al. | 514/21 |
| 5,279,962 | 1/1994 | Gurtler et al. | 435/252.5 |
| 5,523,211 | 6/1996 | Pusztai-Carey et al. | 425/23 |
| 5,662,697 | 9/1997 | Miller et al. | 424/93.2 |
| 5,686,069 | 11/1997 | Payne et al. | 424/93.461 |

FOREIGN PATENT DOCUMENTS

| | | |
|---|---|---|
| 829843 | 12/1966 | Canada . |
| 250908 -A | 1/1988 | European Pat. Off. . |
| A 2 552 627 | 5/1985 | France . |
| 195 03 157 | 2/1995 | Germany . |
| 1043076 | 9/1966 | United Kingdom . |
| A- 2043 448 | 10/1980 | United Kingdom . |
| 2-89 04170 | 5/1989 | WIPO . |
| A-9219102 | 11/1992 | WIPO . |

OTHER PUBLICATIONS

Ignoffo and Batzer, "Microencapuslation and Ultraviolet Protectants to Increase Sunlight Stability of an Insect Virus", J. Econ. Entomol., 64:850–853 (1971).

Smith et al., "Nozzel Size–Pressure and Concentration Combinations for Heliothis Zea Control with an Aqueous Suspension of Polyvinyl Alcohol and *Baculorvius Heliothis*", J. Econ. Entomol. 72:920–927 (1979).

Smith et al., "Laboratory Formulation Comparisons for a Bacteriacl And Vira Insecticide", J. Econ. Entomol. 73: 18–21 (1980).

92–076717/10 (J04021–602–A)—Slow–release pheromone prepn. for insect pest control.

88–002980/01 (J62265927–A) Insecticidal mulching film––comprises laminated film of reflection film layer and black film layer contg. Carbon black.

Bull et al., Improved Formulation of Heliothis Nuclear Polyhedrosis Virus J. Econ. Entomol., vol. 69: 731–736, 1976.

*Primary Examiner*—Neil S. Levy
*Attorney, Agent, or Firm*—Lynn Marcus-Wyner; John D. Peabody, III

[57] ABSTRACT

This invention relates to novel biopesticidal compositions comprising an active insecticidal ingredient selected from insecticidal bacteria and viruses such as *B. thuringiensis* crystal protein or spores or mixtures thereof and baculoviruses such as nuclear polyhedrosis viruses, granulosis viruses and non-occluded viruses; a polymer; and an inorganic light blocking agent wherein the light blocking agent protects the active ingredient from both ultraviolet light and sunlight and the polymer forms a matrix in which the active ingredient and light blocking agent are dispersed therein. Methods for producing the biopesticidal compositions and methods of controlling insects are also included within the scope of the invention.

19 Claims, 1 Drawing Sheet

INSECTICIDAL MATRIX AND PROCESS FOR PREPARATION THEREOF

This is a continuation application of application Ser. No. 08/654,512, filed on Jun. 12, 1996 now U.S. Pat. No. 5,851,545, which claims benefit of U.S. provisional application No. 60/003,336, filed Aug. 25, 1995.

BACKGROUND OF THE INVENTION

Concern over the toxic side effects or lack of specificity of some chemical insecticides has led to the development of biopesticides particularly with insecticidal bacteria and viruses. In general the species *Bacillus thuringiensis* has been the most successful of all microbial biocontrol agents, and strains of *B. thuringiensis* are used as a pesticide in the same manner as chemical control agents. Among the naturally occurring Bacillus protein toxins are the polypeptide crystal toxins. These are active against a variety of insects including lepidoptera insects (particularly, *B. thuringiensis* var. *kurstaki* and *B. thuringiensis* var. *aizawai*); coleoptera insects (particularly, *B. thuringiensis* var. *tenebrionis*); and diptera insects (particularly, *B. thuringiensis* var. *israelensis*). Additionally, viruses particularly baculoviruses such as Heliothis nuclear polyhedrosis virus (NPV) which are effective against Heliothis spp and *Autographa californica* nuclear polyhedrosis virus (NPV) which are effective against alfalfa and *Trichoplusia ni* have been used in biopesticides.

Biopesticides have typically been formulated like chemical pesticides and are usually applied through existing sprayer technology. These formulations may be comprised of the insect pathogen (viruses, such as NPV or bacteria, such as *B. thuringiensis*), spores and/or crystalline delta endotoxins. However, when used in the field, these formulations have a number of disadvantages. When the biopesticide is exposed to sunlight and ultraviolet radiation the effect can be inactivation of the polypeptides comprising the endotoxin and exposure may damage the nucleic acids of the spores rendering the pesticide less effective. Reference is made to Ignoffo et al. Environ. Entomol., 6:411–415 (1977). This decrease in potency of the formulation necessitates numerous repeated applications to susceptible vegetation of the habitat where insect control is desired. A further disadvantage of these biopesticides and particularly, the Bacillus biopesticides is that in low doses they are feeding inhibitory, but they are not lethal. Insects that ingest a sub-lethal, feeding-inhibitory dose cease feeding for a period of time lasting up to several days. This characteristic, when combined with inactivation of the biopesticide by sunlight while the insects are not feeding can lead to poor control of the target insects.

Attempts have been made to solve the sunlight instability problem by providing biopesticidal formulations wherein insecticidal bacteria and viruses are included in the formulation with a sun screening agent. These formulations independently include both encapsulated and nonencapsulated active toxins, but they all suffer from a number of disadvantages. These disadvantages are specific to each formulation. However, general examples with respect to the encapsulated mixtures include: that the polymers forming the walls of the capsules are not always capable of retaining the sun screening agent within the interior of the capsule, in some instances highly toxic materials are used in the capsule preparation; some of the capsules can only be made by processes that are incapable of yielding particles large enough to provide any substantial barrier of sun screening agent (extremely small particles such as those formed from a two-phase liquid emulsion experience substantially uniform sunlight throughout their interiors); and the capsule coating is susceptible to breakdown in the environment.

Disadvantages with respect to nonencapsulated mixtures include that after application through spray equipment to the crop or target location most of the sun screening agent is not normally dose enough to the organism or toxin to be effective; non-encapsulated mixtures also tend to suffer from the disadvantage described above whereby insects ingest sub-lethal feeding-inhibitory doses but later resume their normal feeding.

The present invention overcomes the disadvantages of the prior art compositions and formulations. Active protein toxins are encapsulated or entrapped in a polymer matrix wherein particles are large enough to comprise a dose that is lethal to the target insect. The process of encapsulation is efficient so that the majority of spores and/or crystals comprising the active toxin or ingredient are encapsulated and a low portion of spores and crystals remain nonencapsulated. The component materials of the composition and process do not inactivate the active ingredient of the biopesticide or leave a residue of toxicological concern. The encapsulated particles are stable both during application to the target site and stable in the environment. The active ingredient is released inside the gut of a susceptible insect when ingested. The composition contains a light-blocking agent which is substantially non-toxic and the agent remains inside the composition matrix during and after application to the target site.

SUMMARY OF THE INVENTION

Biopesticidal insecticidally effective compositions, and methods for producing said compositions, are provided for protecting target loci from insect pests. The biopesticides are produced by mixing an active ingredient, insecticidal bacteria or viruses such as spores or insecticidal crystal protein or a combination thereof found in *Bacillus thuringiensis* or baculoviruses, with a polymer and an inorganic light blocking agent wherein the polymer forms a matrix for the active ingredient in combination with the inorganic light blocking agent.

Therefore in a first aspect, the present invention relates to a biopesticidal insecticidally effective composition comprising:

(a) an active ingredient selected from the group of insecticidal bacteria and viruses;

(b) a polymer which is soluble under neutral to alkaline conditions and insoluble under weakly acidic conditions in an aqueous medium wherein the polymer forms a matrix; and (c) an inorganic light blocking agent wherein said light blocking agent is insoluble in water and is dispersed with the active ingredient within the matrix formed by the polymer of (b) and wherein the light blocking agent protects the active ingredient from inactivation by ultraviolet radiation and sunlight.

In a preferred embodiment, the bacteria are *bacillus spp* and the viruses are baculoviruses.

The composition thus formed may be further formulated into an aqueous, dry or non-aqueous final product.

In a second aspect, the present invention relates to a method for preparing a biopesticidal insecticidally effective composition which comprises:

(a) forming a polymer solution wherein said polymer is soluble under neutral to alkaline conditions and insoluble under weakly acidic conditions in an aqueous medium;

(b) forming a dispersion of an inorganic light blocking agent;

(c) obtaining a suspension culture of an insecticidal ingredient selected from the group of bacteria and baculoviruses;

(d) preparing a solution of a volatile base and combining said solution with the suspension culture of step (c);

(e) mixing the dispersion of the light blocking agent with the solution of the polymer to obtain a second dispersion and then combining the second dispersion with the suspension of the active ingredient and solution of volatile base; and (f) spray drying the mixture of (e)

wherein the active ingredient and the light blocking agent are dispersed in a matrix formed by the polymer.

Another embodiment of the invention includes a method for preparing a biopesticidal insecticidally effective composition which comprises:

(a) obtaining a suspension culture of an active ingredient including *Bacillus thuringiensis* insecticidal proteins or spores or a mixture thereof or baculoviruses and mixing an inorganic light blocking agent with the suspension;

(b), forming a polymer solution wherein said polymer is soluble under neutral to alkaline conditions and insoluble under weakly acidic conditions in an aqueous medium wherein the polymer is carboxy polyacrylic acid or a copolymer of styrene mallec anhydride acid comprising about 3 to 10% of the composition;

(c) mixing the mixture of (a) with the solution of (b) to obtain a suspension; and (d) spray drying the suspension wherein the active ingredient and the light blocking agent are dispersed in a matrix formed by the polymer.

In another aspect the invention includes a method of controlling insect pests at a locus where control is desired comprising applying an insecticidally effective amount of the disclosed composition to said locus.

The present invention resides in both the methods described above and the composition thus formed.

DETAILED DESCRIPTION OF THE INVENTION

Figure 1:
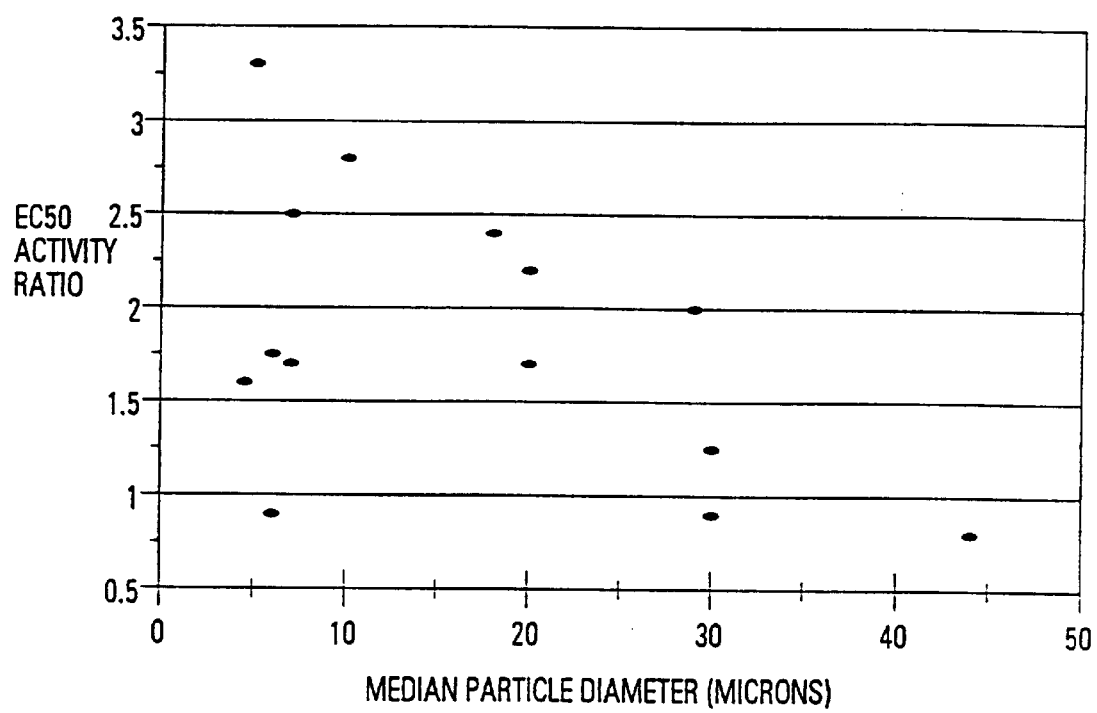
FIG. 1 illustrates the EC50 activity ratio for a composition as described in example 3 versus control samples.

The biopesticidal composition of the invention is composed of three main components, the active insecticidal ingredient; an inorganic light blocking agent; and a polymer component which forms a matrix for the composition.

In a preferred embodiment the active ingredient is obtained from insecticidal Bacillus spp such as *B. thuringiensis, B. popillae*, and *b. sphaericus* in particular *B. thuringiensis*. Insecticidal crystal protein and spores which may be isolated from any *B. thuringiensis* subspecies that is naturally occurring or constructed by recombinant DNA techniques are particularly preferred.

The classification of *B. thuringiensis* is based on biochemical and serological criteria. These divisions correspond to a subspecies or variety with specific phenotypic characteristics. Subspecies of *B. thuringiensis* include *thuringiensis, kurstaki, sotto, dendrolimus, entomocidus, aizawai, morrisoni, tolworthi, israelensis*, and others as disclosed in H.de Barjac and E. Frachon, Classification of *B. thuringiensis* strains, Entomophaga, 35:233 (1990). During sporulation *B. thuringiensis* synthesizes quantities of one or more insecticidal proteins that are organized as crystals. As spores mature the crystals are released into the environment. The genes encoding crystal proteins are well known and designated as cry genes. Numerous cry genes have been isolated and it has been determined that the proteins encoded by these genes differ in terms of insect specificity. Commercially superior *B. thuringiensis* strains may express four or more crystal proteins, and in this respect the crystal protein isolated from the *B. thuringiensis* may include more than one crystal toxin protein.

The invention may include any of the *B. thuringiensis* crystal proteins encoded by various genes such as those enumerated and disclosed in Table 1 of T. Yamamoto and G. Powell in Advanced Engineered Pesticides (ed. Leo Kim) (1993) which is hereby incorporated by reference. The invention also includes active toxins that are engineered. For example a *B. thuringiensis kurstaki* strain which normally exhibits a high level of lepidopteran activity may be engineered to express a coleopteran-active cryIIIA gene. It should be appreciated that any Bacillus active toxin could be used in the invention. However, while not meant to limit the invention in any manner, preferred toxin proteins include CryIA, CryIB, CryIC, CryID, CryIE, CryIF, CryIG, CryII, CryIII, CryIV, CryIH, CryV, CtyA, CytB and any variants, mixtures or parts thereof. Particularly preferred toxins include CryIC, CryIA(a), CryIA(b), CryIA(c), CryIE, CryIIA and variants, mixtures and parts thereof.

Recombinant techniques are well known to those in the art and include conjugation and electroporation to increase the number of toxin proteins a particular Bacillus strain produces and the use of protein design to create a gene expressing a fusion or hybrid protein. An example of a hybrid gene is G27, containing fragments of different Cry proteins and specifically CryIE and CryIC. This protein is further described in Bosch et al., Biotechnology 12:915–918 (1994) which is hereby incorporated by reference. Those skilled in the art are aware of other hybrid genes and the above example is not meant to limit the invention in any manner.

In addition to insecticidal crystal proteins produced by various *B. thuringiensis* strains, the spores produced by said strains may also have insecticidal properties. For example it is known that some spores are effective against insects such as *Galleria mellonella*.

In another preferred embodiment, the active ingredient is a baculovirus. Baculoviruses are a large group of viruses divided into three subgroups: nuclear polyhedrosis viruses (NPV); granulosis viruses (GV) and polydrnavirdae. These viruses infect many insects of which are pests of commercially important agricultural crops.

One of the advantages of baculoviruses is their host specificity. The most widely characterized baculovirus is *Autographa caliornica* nuclear polyhedrosis virus (NPV). This virus is characterized by the formation of viral occlusion bodies in the nuclei of infected host cells. The size of the occlusion bodies varies with the particular subgroup. The occlusion body is a crystalline protein structure wherein the virions are embedded therein.

In the present invention the preferred baculoviruses are strains of *Autographa californica* NPV, *Heliothis zea* NPV, *Spodoptera exigua* NPV, and *Anangrapha falcifera* NPV. As mentioned hereinabove for *Bacillus thuringiensis* recombinant strains of baculovirus are also included within the scope of the invention. Reference is made to The Biology of Baculoviruses, Vol I and II, Granados and Federici eds., CRC Press, Boca Raton, Fla. 1986, for a review of baculoviruses.

The insecticidal active ingredients will comprise about to about 90% by weight of the composition, preferably about 30 to about 80% by weight of the composition and most preferably about 45 to 75% by weight of the composition.

Polymers are generally defined as molecules formed by chemically bonding multiple copies of monomer molecules either in a linear chain or in a branching pattern or some combination of the two. A polymer may be formed exclusively from a single type of monomer, or two or more monomer types may be used. In the present invention the preferred polymers are polyvinyl acetate; poly(acrylic acids) or ester or carboxy derivatives thereof; shellacs; and copolymers of styrene and maleic anhydride and derivatives thereof; and mixtures thereof. Particularly preferred are high molecular weight polymers and co-polymers and most preferred are styrene/maleic anhydride copolymer and carboxy polyacrylic acid.

The polymer which forms the matrix of the composition is defined by the following general characteristics. The polymer must be capable of retaining the light blocking agent. The polymer must be insoluble in the environment to which the treated vegetation is exposed, but must be soluble in the environment of the insect gut which is generally on the alkaline side. Moreover the polymer must not be soluble in the carrier of a formulation if the carrier is a liquid. The polymer must be substantially insoluble in the water used as a carrier in the spray tank and spray equipment. The matrix that the polymer forms must be sufficiently non-friable so that it resists the abrasion and mechanical forces that the composition or end-product formulation experiences during processing and handling.

The pH of the polymer solution should be in the range of about 3.5 to about 9.0 preferably about 5.0 to about 8.0 and most preferably 5.5 to 7.0.

Neutral to alkaline conditions are defined as about pH 6.0 to about pH 11.5, preferably about pH 6.5 to about 11.0. Weakly acid conditions are defined as about pH 6.0 to about pH 4.0 and preferably about pH 5.5 to about pH 4.0. An aqueous media is one wherein water is the solvent.

In general the polymer will comprise about 0.5 to about 25% by weight of the composition preferably about 1 to about 15% by weight of the composition and most preferably about 3–10% of the composition.

The inorganic light blocking agents employed in the compositions of the present invention are those that not only block out ultraviolet radiation, but also block out sunlight and may include light-absorbing agents as well as light reflecting agents. The light blocking agents must be compatible with the polymer material and the active insecticidal ingredients and insoluble in any environment that the composition is expected to encounter prior to ingestion by a susceptible insect.

It has been found that in general stability of a biopesticide to ultraviolet radiation is not a good predictor of stability to sunlight. Some light blocking agents may perform well under ultraviolet light generated by mercury vapor lamps, but provide no protection against solar radiation. Furthermore, in order to be useful and practical, the light blocking agent should function at an amount that can be practically incorporated within a formulation. Materials that do not absorb ultraviolet light or sunlight strongly generally must be used at very large amounts, and thus any particles that are based on such material generally must be large in order to achieve substantial protection against sunlight or ultraviolet light. In general days, metal oxides, and inorganic minerals and dyes that are insoluble in water may be used as light blocking agents of the invention. Two specific types of light blocking agents are particularly useful in the present invention, these include titanium dioxide, a light reflecting agent and carbon black, a light absorbing agent. Additionally melanin and bacteriorhadopsin may be used as light-blocking agents. Combination of these agents may be incorporated into the compositions of the invention.

The light blocking agents comprise about 5 to about 90% by weight of the composition preferably about 5 to about 60% and most preferably about 10 to about 50% by weight of the composition.

As used herein "matrix" means a continuous solid phase composed of the polymer molecules of the invention and containing vacancies, voids or spaces occupied by the other components of the composition. At least approximately 60% of the active ingredient and preferably 60% must be retained within the polymer matrix. The term "dispersed" as used herein means very well mixed so that the individual particles of the light blocking agent or of the active ingredient are substantially uniformly distributed. They may be distributed either in water or the polymer solution as described herein. Furthermore, the particles in suspension are not themselves formed of large aggregates of smaller particles. For this purpose, large aggregates are considered to be those greater than about 5 to about 30 microns in diameter, and preferably about 5 to about 20 microns in diameter.

In a preferred embodiment, the composition comprises an active insecticidal ingredient selected from crystal proteins and spores from *Bacillus thuringiensis*, a carboxy polyacrylic acid polymer or styrene-maleic anhydride co-polymer or a mixture thereof and carbon black, as the light blocking agent. The active ingredients may be obtained from either a naturally occurring strain *B. thuringiensis* or a recombinant strain of *B. thuringiensis* wherein an exogenous crystal encoding toxin gene is expressed. Another preferred embodiment includes the active ingredient selected from *B. thuringiensis* var. *kurstaki*. A further embodiment comprises an active toxin selected from the group consisting of CryIC, CryIA(a), CryIA(b), Cry IIA, CryIA(c) and fragments and mixtures thereof including hybrid proteins.

The biopesticidal compositions of the present invention may be prepared by the following general description.

The insecticidal components of *B. thuringiensis* may be obtained by methods well known in the art, but in general protein and spores to be used in the composition will be produced during a fermentation production process. Fermentation processes are well known and have been described by Bernhard and Utz in Entwistle et al., *Bacillus thuringiensis*, an Environmental Biopesticide, Wiley and Sons, (1993) which is hereby incorporated by reference. The *Bacillus thuringiensis* strains harboring the genes of interest are expressed as active toxins are generally reproduced or multiplied by fermentation in an appropriate nutritive medium comprising a nitrogen source, a carbohydrate source, and mineral salts and adjusted to an appropriate pH of approximately pH7.0. Such fermentation is conveniently effected at a temperature of about 20° C. to about 40° C. from 24 to 72 hours. A suspension concentrate of the *B. thuringiensis* strain can be obtained by evaporation and/or centrifugation of the fermentation liquid to the desired concentration.

The *Bacillus thuringiensis* suspension typically contains about 2 to 10% weight insecticidal crystal proteins and a similar amount of spores. To the *B. thuringiensis* suspension other additives may be included for example, a volatile base such as ammonium hydroxide and a non-volatile acid such as sulfuric add. In a preferred embodiment a solution of ammonium sulfate is prepared and mixed with the active ingredient suspension.

The baculovirus component of the invention may be multiplied by techniques well known in the art and reference is made to Anderson et al., Proc. IV IFS: Ferment. Technol. Today, 623–628, 1972, and Chakraborty, S. et al., Australas. Biotechnol., 5(2), 82–86, 1995 both of which are hereby incorporated by reference.

In general one method includes raising insect larvae susceptible to the particular baculovirus and infecting the larvae with an inoculum of the baculovirus. After the baculovirus infection has run its course the cadavers of the insect larvae are homogenized. In a second general method insect cells are multiplied in a cell culture vessel in a nutritive medium. The vessel is inoculated with an inoculum of baculoviruses. When the baculovirus infection has run its course, the contents of the vessel are harvested and the baculovirus is recovered by centrifugation or filtration.

The polymer solution is prepared by placing the polymer into water at a concentration of about 0.5 to about 20% by weight, raising the temperature to about 60° to about 80° C., preferably to about 70° C., agitating gently and adding aqueous base, preferably ammonium hydroxide or sodium hydroxide over a period of time so that the final pH is about 5.5 to about 8.0, preferably about 7 to about 8. This mixture is then left stirring for several hours or overnight to ensure full dissolution of the polymer. All mixtures and dispersions are preferably achieved using a high shear-intensity mixer.

The pH conditions may be established by various means including mixing appropriate amounts of a volatile base, for example; aqueous ammonia, and a non-volatile acid, for example; sulfuric acid with the polymer solution. The choice of conditions is governed by the need for the polymer to remain in solution prior to spray drying and for sufficient volatile base to be evaporated during spray drying. By combining a suitable amount of non-volatile acid and volatile base in the suspension to be spray dried, the resulting particles of active ingredient and light blocking agent in the polymer matrix have a pH when re-suspended in water that is about 0.5 to about 2.5 pH units lower, and preferably about 1.0 pH unit lower, than the pre-spray suspension. The resulting pH is too acidic for the polymer to readily dissolve and therefore confers physical stability on the particles when suspended in water.

Other additives may be added to the suspension; for example compounds that reduce the tendency of the polymer to undergo a cross-linking and precipitation reaction in the presence of divalent cations, for example, EDTA.

A dispersion of the inorganic light blocking agent in the polymer solution is prepared by adding water to the polymer solution and optionally a dispersant such as lignosulfate. Dispersants are well known in the art. The light blocking agent is then added to the mixture and mixed with preferably a high shear mixer.

The resulting mixture is spray dried, causing the evaporation of most of the water and volatile base. The spray dryer may be controlled in a conventional manner to obtain particles with diameters in the size range of 1 to 50 microns, with a preferred medium (volume averaging) in the range from about 10 to 40 microns. It is also preferred that the particle size distribution be relatively narrow, so that at least 60% of particles and more preferably 80% of the particles have sizes at or close to the median diameter.

It should be emphasized that the compositions of the invention may include other conventional agents and additives. Such agents include but are not limited to surface-active agents; such as octylphenol ethoxylate, stabilizers; such as propionic acid, filling agents; such as de-fatted soyflour, flowability or anti-caking agents; such as synthetic precipitated silica, dispersants; such as sodium salt of condensed naphthalene sulfonic acid and the like. The quantity of surface-active agents can vary over a wide range. For convenience such agents may comprise from about 0.1% to about 50% by weight of the composition, more preferably about 0.5% to about 40% and most preferably 1% to about 20%.

The compositions of the present invention may be further formulated, and one skilled in the art is aware of many methods for producing formulated biopesticidal products. These methods are described in the technical and patent literature and include methods for forming granules, wettable powders, water-based and oil-based flowables, concentrates and the like. The following examples are provided for illustration and are not meant to limit the invention in any way.

A. Wettable powder formulation: 63% active insecticidal ingredients, 10% flow agent (precipitated silica), 4% surfactant (naphthalene sulfonate), 13% dispersant (alkylarylpolyoxy acetate), 7% carrier (attapulgite day), and 3% sequestrant (EDTA).

B. Granule: 63% active insecticidal ingredients, 20% flow agent (precipitated silica), 3% surfactant (linear alkyl benzene sulfonate), 5% dispersant (blend of anionic surfactant and sodium lignosulfonate), and 9% carrier (kaolin clay).

The compositions of the present invention containing the active insecticidal ingredients and any further formulations may be used in a method of controlling insect pests at a locus where control is desired comprising applying an insecticidally effective amount of the composition to a locus wherein said locus includes but is not limited to a crop plant or insect habitat. Target loci which are potential habitats for Lepidoptera, Diptera and Coleoptera insects include but are not limited to the following: cereals; such as wheat, corn, rice, and barley; cotton; leguminous plants; oil plants such as sunflowers; vegetable crops; deciduous and conifer trees; orchard and vine crops; and fresh water bodies. An insecticidally effective amount is that amount of active ingredient which causes substantial mortality of the insect to be controlled.

The formulations may be water dispersible and may be further diluted with water before they are applied. The appropriate concentrations, dilutions as well as appropriate timing and method of application in each case will depend on the nature of the pathogen to be controlled and the type of vegetation to be treated and will be readily apparent to those skilled in the art.

The following examples more fully illustrate specific embodiments of the invention. As will be recognized by one skilled in the art, these examples are illustrative and are not meant to be limiting. Additionally, in each example 1A through D at least ten replicate compositions were prepared using the stated components or minor variations thereof.

EXAMPLE 1

BIOPESTICIDAL COMPOSITIONS

A. Carbon black and carboxy polyacrylic acid:

Eighty-nine grams (g) of water are heated to 70° C. and 10 g of carboxypolyacrylic acid (Carboset 525, BF Goodrich) are added under gentle agitation. 1 g of 30% aqueous ammonium hydroxide is added in 5 equally spaced and sized aliquots over a period of 4 hours. This solution (I) is allowed to stir overnight.

Ten g of carbon black (Printex P, Degussa) is added to 90 g of water and mixed with a high shear-intensity mixer for 3 hours. The pH of this carbon black dispersion (II) is adjusted to 2.0 with 25% aqueous sulfuric acid.

Sixteen g of dispersion (II) is added to 4 g of solution (I) and mixed with a high shear-intensity mixer for at least 30 minutes to create a dispersion of carbon black in polymer solution (III) with a pH between about 5.9 and 6.4. Eight g of powder preparation of B. thuringiensis var. kurstaki strain SA 12 spores and crystals, containing CryIA(c) and CryIA (b) are mixed with 72 g of water and allowed to stir for 2 hours. The pH of this suspension is adjusted to 4.2 with 25% aqueous sulfuric acid and then to 5.0 with 30% aqueous ammonium hydroxide. This pH adjustment procedure is repeated 2 more times. The pH of the B. thuringiensis suspension is adjusted to 0.1 units above that of preparation (III) with 30% aqueous ammonium hydroxide, and the two are mixed together with a high shear-intensity mixer for at least 45 minutes. The resulting mixture is spray dried with a Buchi 190 Mini Spray Dyer with an inlet air temperature of about 180° C., a reduced air pressure of about 52 mbar, a spray rate of about 10 mL/min, atomization air pressure at 4 bar and the spray nozzle adjusted to obtain a narrow size distribution with a median diameter of about 10 to 20 microns. The samples have a half-life under sunlight of about 20 mW-hrs/cm$^2$ (measured at 360 nm), compared to about 10 mW-hr/cm$^2$ for samples containing no carbon black but otherwise identical. The method for measuring half-lives has been described by Fowler et al. in Photostability Preparation of B. thuringiensis and Use of Light-Absorbing Protectants, Eighth IUPAC International Congress on Pesticide Chemistry, July 1994, Wash. D.C., which is hereby incorporated by reference.

B. Titanium dioxide and carboxy polyacrylic acid

A polymer solution (I) is prepared as described in Example 1A. 4.2 g of powder preparation of B. thuringiensis var kurstaki strain SA 12 spores and crystals are mixed with 79.2 g of water and allowed to stir for 2 hours. The pH of this suspension is adjusted to 4.2 with 25% aqueous sulfuric acid and then to 6.2 with 30% aqueous ammonium hydroxide. This pH adjustment procedure is repeated 2 more times before adjusting the pH to 6.5 with 30% aqueous ammonium hydroxide.

4.6 g of titanium dioxide (Tronox, Kerr-McGee) is added to the B. thuringiensis suspension and mixed with a high shear-intensity mixer to create a dispersion (IV). 0.4 g of EDTA is mixed with 3.6 g of water and added to dispersion (IV). Immediately thereafter, 8 g of polymer solution (I) is added and mixed with a high shear-intensity mixer for at least 45 minutes. The resulting mixture is spray dried as in Example 1A. The samples have a half-life under sunlight of about 20 mW-hrs/cm$^2$ compared to 10 mW-hrs/cm$^2$ for samples containing no titanium dioxide but otherwise identical.

C. Carbon black and styrene/Maleic anhydride co-polymer

Ten g of styrene/maleic anhydride copolymer (Scripset 520, Monsanto) are added to 83.2 g of water under gentle agitation. 6.8 g of 30% aqueous ammonium hydroxide are added in 10 equally spaced and sized aliquots over a period of 5 hours. This solution (V) is allowed to stir overnight. 10 g of carbon black is added to 90 g of water and 0.2 g of 98% sulfuric acid and mixed with a high shear-intensity mixer for 3 hours to form a dispersion (VI). 16 g of dispersion (VI) is added to 4 g of solution (V) and mixed with a high shear-intensity mixer for at least 30 minutes to create a dispersion of carbon black in polymer solution (VII) with a pH between about 5.9 and 6.4.

Eight g of powder preparation of B. thuringiensis var. kurstaki strain SA 12 spores and crystals are mixed with 72 g of water and allowed to stir for 2 hours. The pH of this suspension is adjusted to 4.2 with 25% aqueous sulfuric acid and then to 6.3 with 30% aqueous ammonium hydroxide. The pH of the B. thuringiensis is then adjusted to 0.1 units above that of the preparation (VII) with 30% aqueous ammonium hydroxide, and the two are mixed together with a high shear intensity mixer for at least 45 minutes.

The resulting mixture is spray dried with conventional spray drying equipment, controlling the process to obtain a narrow size distribution with a median diameter of about 10 to 20 microns. Samples have a half-life under sunlight of about 20 mW-hrs/cm$^2$, compared to about 10 mW-hr/cm$^2$ for samples containing no carbon black but otherwise identical.

D. Carbon black and carboxypolyacrylic acid:

A polymer solution (I) is prepared by adding 4 g of carboxypolyacrylic acid (Carboset 525, B.F. Goodrich) to 22.7 g of water, raising the temperature to about 70° C., agitating gently and adding concentrated sodium hydroxide over a period of about 1 to 8 hours so that the final pH is about 7 to 8. This mixture is then left stirring for several hours or overnight to ensure full dissolution of the polymer. A dispersion (II) of carbon black (Printex G, Degussa) in a polymer solution is prepared by adding 197.3 g water to the polymer solution (I), adding 0.66 g of lignosulfonate or similar dispersant (such as Tamol SN of Rohm & Haas, Philadelphia, Pa. or Polyfon H o Westvaco, Charleston Heights, S.C.) adding 33 g of carbon black and mixing with a high shear mixer. A solution of ammonium sulfate (III) is prepared by dissolving 4.2 g of salt into 30 g of water. Sixty-three g of powder preparation of B. thuringiensis var. kurstaki strain SA12 spores and crystals are mixed with 500 g of water and allowed to stir for 2 hours. This Bt suspension (IV) is mixed with the ammonium sulfate solution in (III) and the pH is adjusted to 6.3 with concentrated sodium hydroxide or concentrated sulfuric acid as necessary. A pre-spray slurry (V) is prepared by mixing together the Bt suspension in (IV) with the dispersion of carbon black in a polymer solution in (II). The pre-spray slurry is spray dried as described in Example 1A above. The samples have a half-life under sunlight of about 100 mW-hrs/cm$^2$ compared to 10 mW-hrs/cm$^2$ for samples containing no carbon black but otherwise identical.

E. Carbon black and styrene/maleic copolymer

A preparation is made of Autographa californica nuclear polyhedrosis virus (NPV) as an aqueous suspension of 5.4% total solids. Carbon black (Norit A), 100 g is dispersed in 395 g water with 5 g dispersant (Morwet, Witco Corp) by pebble milling overnight. The dispersion, 66.1 g is then mixed with 66.1 g of the NPV suspension and the pH is adjusted to 8.6 to yield a second dispersion. A solution of styrene/maleic anhydride copolymer is prepared as described in Example 1C except with 200 g water. The polymer solution is mixed with the second dispersion and the resulting mixture is spray dried as described in Example 1A.

EXAMPLE 2

Pesticidal Activity

Samples are prepared as described in Example 1C above except at a range of different median particle sizes, ranging from about 4 to 45 microns by varying spray drying conditions. The reduced air pressure is varied from about 52 to about 43 mbar, the spray rate is varied from about 10 to about 7mL/min, and the spray nozzle adjusted to obtain the desired narrow size distributions. The samples are suspended in water with 0.2% surfactant (Sylard 309, Dow Coming) and sprayed onto broad leaf cabbage plants at the 6 to 10 leaf stage. After the deposits have dried, leaves are collected and infested with late first instar *Trichoplusia ni* larvae. After 4 days incubation, mortalities are measured and the EC50's are determined using the probit calculation method described by Finney, D. J., Probit Analysis, Cambridge University Press (1964) (see FIG. 1). EC50 is defined as the concentration causing 50% mortality (death). This figure illustrates the increased activity that is achieved by the present invention in comparison with control samples that do not include polymer to prevent individual spores and crystals from spreading over the leaf surface and thereby presenting sub-lethal feeding-inhibitory doses.

EXAMPLE 3

Efficacy and Persistence Of Insecticidal Activity.

Samples are prepared as described in Example 1A above, but with the quantities modified as follows: 4 g of solution (I) are mixed with 48 g of dispersion (II), and 4.8 g of *B. thuringiensis* powder are mixed with 43.2 g of water. The resulting spray dried powder (VIII) is suspended in water and sprayed onto a cabbage at an application rate equivalent to 0.33 lb/ac *B. thuringiensis* in the same manner as described in example 2. A control sample not containing carbon black or polymer is also sprayed on cabbage at a rate equivalent to 0.85 lb/ac *B. thuringiensis*. The plants are exposed to sunlight, and leaves are collected and infested with *T. ni* larvae. The mortalities (corrected with respect to untreated plants) as a function of days sunlight exposure are illustrated in Table 1.

TABLE 1

| Days Exposure to Sunlight | Mortality (%) | |
|---|---|---|
| | Encapsulated | Un-encapsulated |
| 0 | 100 | 100 |
| 2 | 97 | 78 |
| 3 | 100 | 48 |
| 4 | 93 | 37 |
| 5 | 100 | 37 |
| 6 | 83 | 10 |
| 7 | 78 | 0 |
| 8 | 80 | — |

EXAMPLE 4

Persistence

When the mixture (IX) *B. thuringiensis* and carbon black in a 1:1 mixture is sprayed onto glass plates at a concentration of 10% total solids and at a spray rate equivalent to 30 g/ac, the half-life under sunlight is about 26 mW-hrs/cm$^2$. When the concentration is reduced to 1% total solids the half-life dropped to about 15 mW-hrs/cm$^2$. At this low level of solids on the glass plate there is insufficient carbon black in dose proximity to the *B. thuringiensis* preparation to provide effective protection against sunlight-the remaining light blocker layer is not thick enough to absorb a significant portion of the incident radiation. In a typical agricultural use, a pesticide must be effective when sprayed at total solids concentration not exceeding 1% in order to have any practical utility.

A sample is then prepared as described in Example 1C above and it is sprayed onto glass plates at a concentration of 1% total solids and at a spray rate equivalent to 30 ga/ac. The half-life under sunlight is greater than 130 mW-hrs/cm$^2$. This result demonstrates the utility of the polymer matrix in retaining the spores and crystals of the *B. thuringiensis* preparation in intimate contact with the particles of the inorganic light blocking agent, and how the composition provides effective protection against inactivation by sunlight.

It is claimed:

1. A biopesticidal insecticidally effective composition comprising;
    (a) an active ingredient selected from the group consisting of insecticidal bacteria, insecticidal viruses, insecticidally active proteins produced from said bacteria and insecticidally active proteins produced from said viruses;
    (b) a polymer which is soluble under neutral to alkaline conditions and insoluble under weakly acidic conditions in an aqueous medium wherein the polymer forms a matrix;
    (c) an inorganic light blocking agent wherein said light blocking agent is insoluble in water and is dispersed with the active ingredient within the matrix formed by the polymer of (b) and wherein the light blocking agent protects the active ingredient from inactivation by ultraviolet radiation and sunlight; and
    wherein said composition is in the form of spray dried particles, said particles having a median particle diameter of 10–30 microns.

2. The composition according to claim 1 wherein the active ingredient is *Bacillus thuringiensis* crystal protein or spores or a combination thereof.

3. The composition according to claim 1 wherein the active ingredient comprises about 30 to about 80%, the polymer comprises about 1 to about 15% and the inorganic light blocking agent comprises about 5 to about 60% by weight of the composition.

4. The composition according to claim 1 wherein said active ingredient is derived from a recombinant strain of Bacillus.

5. The composition according to claim 1 wherein said active ingredient is derived from a naturally occurring strain of Bacillus.

6. The composition according to claim 2 wherein the active ingredient is a *Bacillus thuringiensis* crystal protein selected from the group consisting of CryIC, CryIA(a), CryIA(b), CryIA(c), CryIIA and CryIE proteins and mixtures or parts thereof.

7. The composition according to claim 1 wherein the polymer is carboxy polyacrylic acid or styrene maleic anhydride copolymer.

8. The composition according to claim 1 wherein the inorganic light blocking agent is carbon black, titanium dioxide or a mixture thereof.

9. The composition according to claim 1 wherein the active ingredient is a baculovirus protein.

10. The composition according to claim 1 wherein said composition is further formulated as a granule, wettable powder, water-based flowable formulation or oil-based flowable formulation.

11. A method of controlling insect pests at a locus where control is desired comprising applying an insecticidally effective amount of the composition of claim 1 to said locus.

12. The method according to claim 11 wherein the insect pest is a Lepidoptera insect pest.

13. The method according to claim 11 wherein the insect pest is a Coleoptera insect pest.

14. The composition according to claim 1 wherein said active ingredient is derived from a strain of *Bacillus thuringiensis* var. *kurstaki*.

15. The composition according to claim 1 wherein said active ingredient is derived from a strain of *Bacillus thuringiensis* var. *aizawai*.

16. A composition according to claim 1, wherein said polymer is selected from the group consisting of polyvinyl acetate, carboxy polyacrylic acid, ester derivatives of poly (acrylic acids), carboxy derivatives of poly(acrylic acids); shellacs; copolymers of styrene and maleic anhydride, styrene/maleic anhydride copolymer; and mixtures thereof.

17. A method according to claim 16, wherein said polymer is styrene/maleic anhydride copolymer or carboxy polyacrylic acid.

18. A composition according to claim 1 wherein said median particle diameter is 10 to 20 microns.

19. A composition according to claim 1 wherein there is a particle size distribution, said particle size distribution is that of at least 60% of the particles having diameters at or close to the median particle diameter.

* * * * *